United States Patent
Etzkorn et al.

(10) Patent No.: US 12,191,015 B1
(45) Date of Patent: *Jan. 7, 2025

(54) SYSTEMS AND METHODS FOR MONITORING MEDICAL ADHERENCE AND COMPLIANCE

(71) Applicant: Verily Life Sciences LLC, South San Francisco, CA (US)

(72) Inventors: James Etzkorn, Mountain View, CA (US); Todd Whitehurst, Belmont, CA (US); Brian Marc Pepin, San Francisco, CA (US); Robert Francis Wiser, San Francisco, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 562 days.

This patent is subject to a terminal disclaimer.

(21) Appl. No.: 16/947,420

(22) Filed: Jul. 31, 2020

Related U.S. Application Data

(63) Continuation of application No. 15/097,675, filed on Apr. 13, 2016, now Pat. No. 10,769,245.

(51) Int. Cl.
  *G16H 10/60* (2018.01)
  *G16H 20/10* (2018.01)
  *H04W 4/80* (2018.01)

(52) U.S. Cl.
  CPC ............ *G16H 20/10* (2018.01); *G16H 10/60* (2018.01); *H04W 4/80* (2018.02)

(58) Field of Classification Search
  CPC .......... G16H 20/10; G16H 10/60; H04W 4/80
  See application file for complete search history.

(56) References Cited

U.S. PATENT DOCUMENTS

| | | | |
|---|---|---|---|
| 3,227,127 A | 1/1966 | Robert et al. | |
| 3,410,450 A | 11/1968 | Fortenberry | |
| 4,711,368 A | 12/1987 | Simons et al. | |
| 5,406,263 A | 4/1995 | Tuttle | |
| 7,877,268 B2 | 1/2011 | Kulkarni | |
| 8,508,346 B2 | 8/2013 | Heath et al. | |
| 8,698,627 B2 | 4/2014 | Haraldsson et al. | |
| 9,770,390 B2 | 9/2017 | Aggarwal et al. | |
| 2005/0241983 A1 | 11/2005 | Snyder et al. | |
| 2009/0301925 A1* | 12/2009 | Alloro | A61J 7/0481 206/534 |
| 2015/0286852 A1* | 10/2015 | Sengstaken, Jr. | A61J 7/04 340/10.1 |
| 2016/0026773 A1* | 1/2016 | Chu | G01L 5/00 705/2 |

(Continued)

OTHER PUBLICATIONS

U.S. Appl. No. 15/097,675, Advisory Action, Mailed On Nov. 25, 2019, 5 pages.

(Continued)

*Primary Examiner* — Maroun P Kanaan
(74) *Attorney, Agent, or Firm* — Kilpatrick Townsend & Stockton LLP

(57) ABSTRACT

A medication packet bundle includes one or more beacons. Each beacon may transmit a signal representing an event related to patient compliance with a medication regimen, such as removal of a packet of medication from a bundle or opening of a packet. The transmitted beacon signals can be monitored and processed to track patient compliance and adherence.

26 Claims, 4 Drawing Sheets

(56) References Cited

U.S. PATENT DOCUMENTS

2017/0020785 A1   1/2017   McCullough

OTHER PUBLICATIONS

U.S. Appl. No. 15/097,675 , Final Office Action, Mailed On Aug. 21, 2019, 13 pages.
U.S. Appl. No. 15/097,675 , Non-Final Office Action, Mailed On Jan. 9, 2020, 14 pages.
U.S. Appl. No. 15/097,675 , Non-Final Office Action, Mailed On Feb. 8, 2019, 7 pages.
U.S. Appl. No. 15/097,675 , Notice of Allowance, Mailed On May 5, 2020, 14 pages.

* cited by examiner

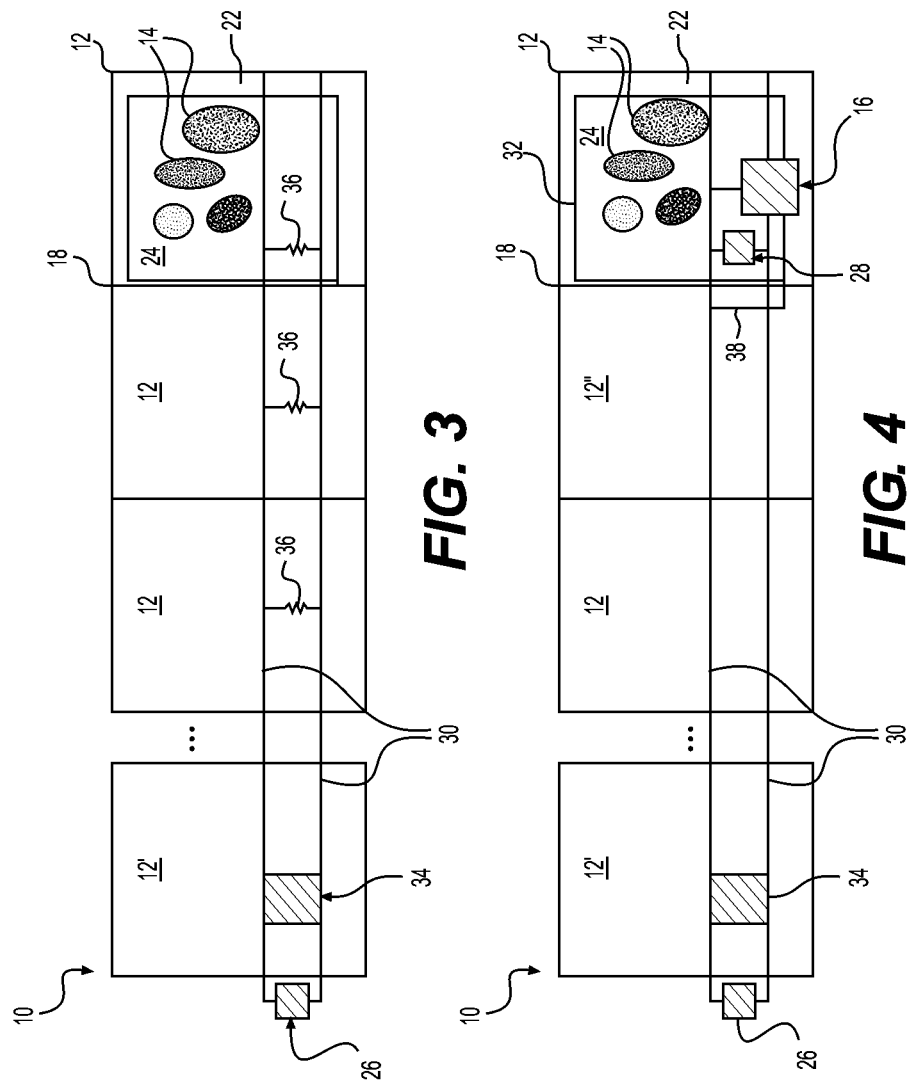

SYSTEMS AND METHODS FOR MONITORING MEDICAL ADHERENCE AND COMPLIANCE

CROSS-REFERENCE TO RELATED APPLICATIONS

This application is a continuation of co-pending U.S. patent application Ser. No. 15/097,675, filed Apr. 13, 2016, titled "Systems and Methods for Monitoring Medical Adherence and Compliance," the entirety of which is hereby incorporated by reference.

BACKGROUND

The present disclosure generally relates to systems and methods for monitoring medical adherence and compliance. More particularly, and without limitation, the disclosed embodiments relate to smart packaging of medications allowing monitoring of a patient's use of medication.

Medication adherence is the act of timely filling or refilling prescriptions for medications. Medication compliance is the act of taking medication on schedule or as prescribed by a physician. According to the National Council on Patient Information and Education, poor medication adherence can lead to unnecessary disease progression and complications, reduced functional abilities and quality of life, additional medical costs and physician visits, increased use of expensive, specialized medical resources, and unneeded medication changes. Medication noncompliance can also lead to adverse effects—the average length of hospital stays due to medication noncompliance is 4.2 days. In the United States, 12 percent of people are 0% compliant (i.e., do not take their medication at all) even after they fill the prescription (i.e., are adherent).

There are a number of reasons why people are nonadherent and/or noncompliant with their medication regimen. The various factors that interfere with medication adherence and compliance include: social/economic-related factors such as age, race, economic status, literacy and costs; individual factors such as forgetfulness, treatment anxiety, misunderstood instructions and fear of addiction; medication-related factors such as the length or complexity of the treatment and the side-effects of the medication; and condition-related factors such as comorbidities and disabilities, and the overall severity of the condition.

By some estimates, up to 50% of patients are noncompliant to some extent, making it difficult for doctors to assess if a medication regimen is effective. If the patient is not accurately or truthfully reporting his or her compliance, doctors do not have a means of obtaining more accurate information. Furthermore, patient tracking of which medications to take and when can be cumbersome and can be confusing for some patients.

There are various techniques and systems for assisting patient adherence. For instance, processes are known for electronically transmitting prescriptions to a pharmacy, and the pharmacy automatically delivering the medication to the patient or sending reminders to the patient. Certain packaging is also known for aiding patient compliance, for example the PILLPACK available from PillPack, Inc. While these prior art approaches help the patient achieve compliance, doctors still do not know if the patient ever opens the package or takes the medication as prescribed.

SUMMARY

Embodiments of the present disclosure include systems and methods for monitoring medical adherence and compliance. Embodiments of this disclosure include, for example, pill packages with beacon transponders in a package of medication.

In some embodiments of the present disclosure, the beacon is a low-energy radio transponder. In an exemplary embodiment, the beacon is a BLUETOOTH Low Energy (BLE) transponder, such as a BLUETOOTH Smart or BLUETOOTH 4.0. Other protocols are also usable such as passive WiFi, ZIGBEE, 6LoWPAN or Z-Wave. In illustrative embodiments of the present disclosure, the beacon can be activated when a medication package is opened, and is programmed to transmit the contents of the package for a period of time to a smartphone or other device enabled to receive the beacon's signals. The smartphone or other enabled device can be detected by a beacon when it comes in range and open communications, using for example Proximity Beacon application program interface (API) and Eddystone protocol available from Google. As will be appreciated from this disclosure, other communication protocols may be utilized.

According to an example embodiment of the present disclosure, a medication package system is described having a packet bundle comprising a plurality of packets of medication, and a beacon system including a power source that powers at least one beacon, the beacon transmitting a signal when a packet of medication is separated from the packet bundle.

According to an additional example embodiment, a packet bundle is described having a plurality of individual sealed packets frangibly connected in a continuous arrangement, at least one of the plurality of sealed packets comprising a local power source; a central power source connected to one or more central power conductors extending across the plurality of packets; and a beacon connected to the local power source and the central power source; wherein, when one of the central power conductors is severed by separating a packet from the central power source, the beacon remains connected to the local power source and transmits a signal indicating that the packet has been separated from the packet bundle.

According to a still further example embodiment, a packet bundle is described having a plurality of individual sealed packets frangibly connected to one another in a continuous arrangement; a central power source connected to central power conductors extending across the plurality of packets; and a central beacon connected to the central power source, the central beacon being provided on at least one of the plurality of sealed packets; wherein, when one of the central power conductors is severed by separating a resistor from the central power source, the beacon transmits a signal indicating that a packet has been separated from the packet bundle based on a change of resistance.

According to a yet further example embodiment, a packet bundle is described having a plurality of individual sealed packets frangibly connected to one another in a continuous arrangement, a central power source connected to central power conductors extending across the plurality of packets; a local beacon provided on at least one of the plurality of sealed packets, the local beacon being connected to a local power source and the central power source; and a central beacon connected to the central power source; wherein, when one or more of the central power conductors are severed by separating a packet from the central power source, the local beacon remains connected to the local power source and the central beacon transmits a signal indicating that the packet has been separated from the packet bundle; and further wherein, when a frangible feature for detecting the packet seal has been broken is severed, the local beacon transmits a signal indicating that the packet has been opened.

According to a still further example embodiment according to the present disclosure, a method for monitoring use of a packet bundle of medication is described, the method including detecting when a packet of medication is separated from the packet bundle; and transmitting, based on the detection, a signal from a beacon that indicates the separation of the packet from the bundle.

According to further aspects of the present disclosure, the beacon may transmit a unique identifier that can be decoded to reveal the pill regimen, using a networked resource, or the entry of a proper key or password from the user.

According to an example embodiment, a small battery is included in the packaging to power a circuit to detect when a packet is opened and to transmit beacon signals.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 3 is a schematic representation of an exemplary medication packet bundle including a central beacon, consistent with the disclosed embodiments.

FIG. 4 is a schematic representation of another exemplary medication packet bundle including beacons, consistent with the disclosed embodiments.

DETAILED DESCRIPTION

The disclosed embodiments relate to medication packages including beacons signaling when a medication package has been opened by a user. As a result, the beacon's signals can be monitored to indicate patient compliance with a medical regimen.

Reference will now be made in detail to embodiments of the present disclosure, examples of which are illustrated in the accompanying drawings. Where possible, the same reference numbers will be used throughout the drawings to refer to the same or like parts.

Figure 1:
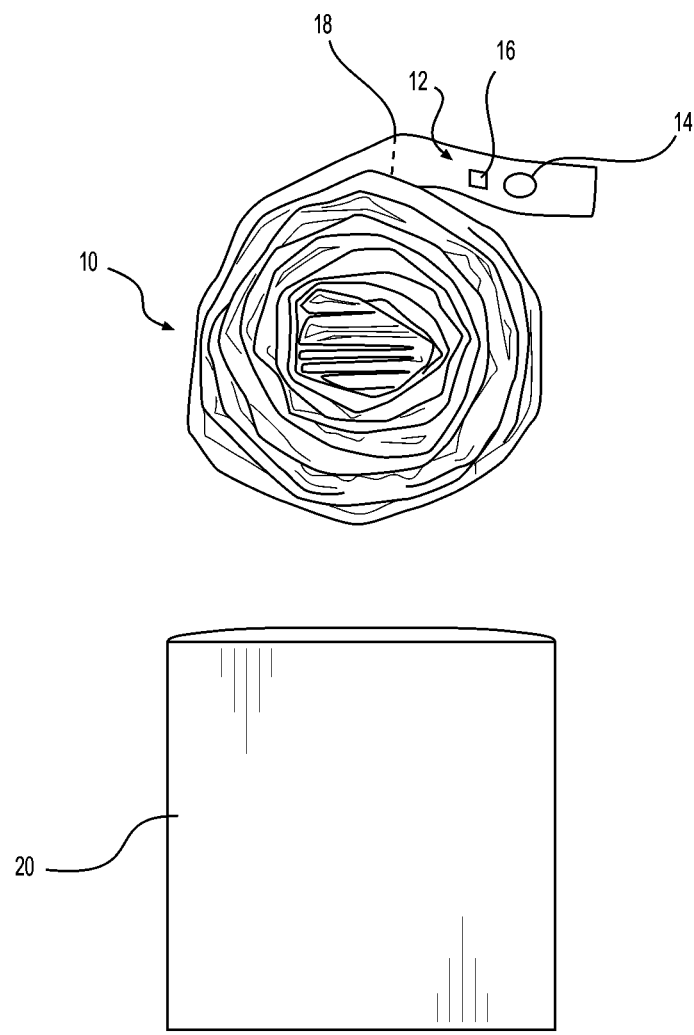
FIG. 1 depicts an exemplary medication packet bundle and package including beacon capability, according to aspects of the present disclosure.

FIG. 1 depicts an example embodiment of a packet bundle 10 which in an illustrative embodiment is a segmented roll of individual packets 12 containing medication such as pill 14. While shown as a continuous reel in FIG. 1, other continuous formats can be employed, including ammo-pack and fan-fold, as well as sheets having a plurality of packets 12. Each packet 12 permits a beacon system to be employed to track when packet 12 is separated from packet bundle 10. In the illustrative embodiment, beacon 16 is depicted associated with packet 12, but other beacon features can take other configurations as discussed below. Each packet 12 is shown as being separable from bundle 10 by way of a frangible feature, which in an illustrative embodiment takes the form of tear line 18. The tear line 18 may be perforated or otherwise prepared to enable separation of each packet 12 from bundle 10. The packet bundle 10, in the example embodiment in the form of a reel, can be received and stored in an outer packaging 20. By way of example, outer packaging 20 may be implemented in the form of a carton or box.

Figure 2:
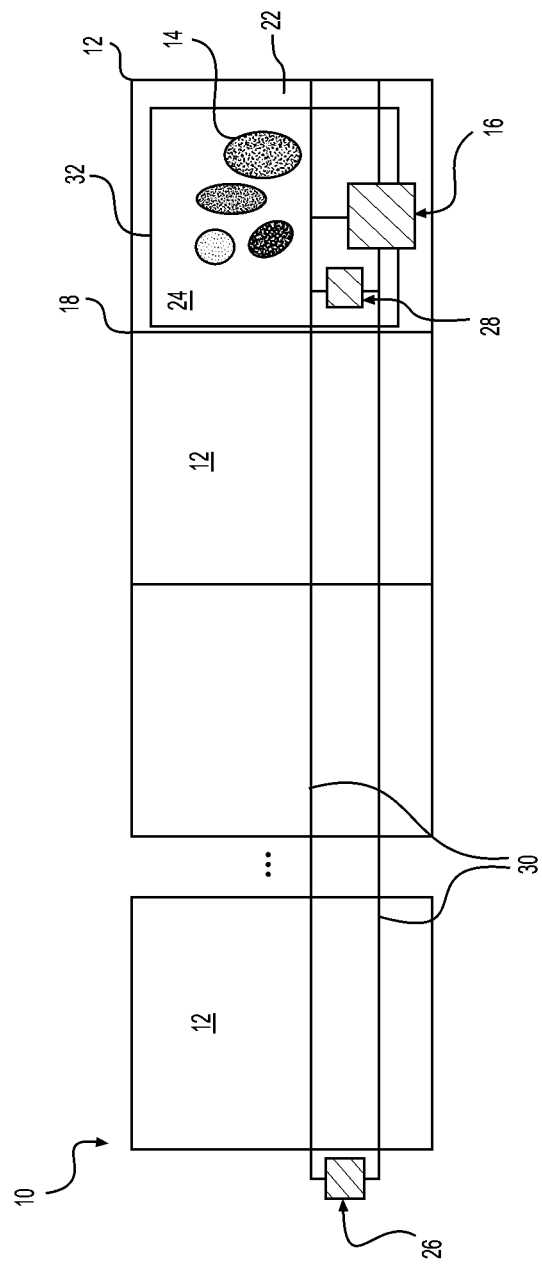
FIG. 2 is a schematic representation of an exemplary medication packet bundle including individual packet beacons, consistent with the disclosed embodiments.

Turning to FIG. 2, a schematic representation of packet bundle 10 according to an example embodiment of the present disclosure is shown. Packet bundle 10 is shown having a plurality of packets 12 in series. In an alternative embodiment, the packets could be arranged in an i×j matrix of strips. Seal margin 22 creates a sealed space 24 in the form of an envelope to contain medication 14, comprising for example one or more pills, tablets, capsules, suppositories, ampoules, subpackets of powder, etc.

According to an illustrative embodiment, central power source 26, which can take the form of a battery, is connected to central power conductors 30 that extend in parallel across packets 12. Local power source 28, which in illustrative embodiments is a battery, capacitor, or other power storage device, is operatively connected to beacon 16. When connected to the packet bundle 10, the beacon remains in low-power standby mode, but when the central power conductors 30 are severed by separating packet 12 along tear line 18, an interrupt occurs causing beacon 16 to signal that it has been separated from the packet bundle 10 and central power source 26. In an example embodiment, packet 12 has a packet periphery conductor 32, which is illustrated taking the form of a conductive trace surrounding the sealed space 24. When packet 12 is opened to access the medication 14, for example by tearing, the periphery conductor 32 is broken, which is detected by beacon 16, causing beacon to signal that packet 12 has been opened. This signal is received by a smartphone or other associated device, which can use the event as evidence that patient has taken the medication in compliance monitoring.

When a beacon 16 as disclosed herein broadcasts data, the data can be sent in advertising packets through one or more wireless advertising channels. The transmission of advertising packets takes place periodically during advertising events. Within an advertising event, the beacon can sequentially use each advertising channel for packet transmission. In some embodiments, an associated device scans these advertising channels for the presence of advertising packets from the beacon. The transmissions from the beacon to an associated device can also take place over a bidirectional data communication link. The creation of such a connection can include a beacon announcing over advertising channels that it is a connectable device, while the associated device listens for such advertisements. When the associated device finds a beacon, it may transmit a connection request message to the beacon, which establishes a point-to-point connection between the two devices. The packets for this connection can be identified by an access code for security. In other embodiments, the beacon can send advertising packets without connecting to an associated device. In this case, the transmissions are undirected and broadcast to all devices in a vicinity.

In some embodiments, beacon 16 can broadcast encrypted data. In some examples, packet bundle 10 and/or packets 12 can include an encryption key, such as a QR code. A smartphone, or other device, can be used to scan the code, otherwise receive the encryption key, and use the key to receive encrypted data from beacon 16. In this way, only authorized devices may receive broadcasts from beacon 16, which can increase security, for example when undirected transmissions are used.

Turning to FIG. 3, a schematic representation of packet bundle 10 with a central beacon, according to an example embodiment of the present disclosure is shown. Packet bundle 10 is shown having a plurality of packets 12' and 12 in series. In an alternative embodiment, the packets could be arranged in an i×j matrix of strips. Seal margin 22 creates a sealed space 24 in the form of an envelope to contain medication 14, comprising one or more pills, tablets, capsules, suppositories, ampoules, subpackets of powder, etc.

According to an illustrative embodiment, central power source 26, which can take the form of a battery, is connected to central power conductors 30 that extend in parallel across packet 12' and packets 12. In packet 12', a central beacon 34 is disposed. Each other packet 12 is provided with a resistor 36. The resistors 36 are wired in parallel such that the total resistance of the packet bundle 10 is proportional to the number of packets. When the central power conductors 30 are severed by separating a packet 12 along tear line 18, a change in the circuit resistance occurs causing central beacon 34 to signal that one or more packets 12 have been separated from the packet bundle 10 and central beacon 34. This signal is received by a smartphone or other associated device, which can use the event as evidence that patient has taken the medication in compliance monitoring.

Turning to FIG. 4, a schematic representation of packet bundle 10 according to an example embodiment of the present disclosure is shown. Packet bundle 10 is shown having a plurality of packets 12', 12, 12" and 12 in series. In an alternative embodiment, the packets could be arranged in an i×j matrix of strips. Seal margin 22 creates a sealed space 24 in the form of an envelope to contain medication 14, comprising one or more pills, tablets, capsules, suppositories, ampoules, subpackets of powder, etc.

According to an illustrative embodiment, central power source 26, which can take the form of a battery, is connected to central power conductors 30 that extend in parallel across packet 12' and packets 12, 12", and 12. In packet 12', a central beacon 34 is disposed. Local power source 28, which in illustrative embodiments is a battery, capacitor, or other power storage device, is operatively connected to beacon 16. Beacon 16 is also connected to central power conductors 30. Central power source 26 and local power source 28 are both therefore connected to beacon 16. In an example embodiment, centralized beacon 34 can broadcast when the package is removed from the packet bundle 10 along tear line 18, severing central power conductors 30. In an example embodiment, packet 12 has a packet periphery conductor 32, which is illustrated taking the form of a conductive trace surrounding the sealed space 24. When packet 12 is opened to access the medication 14, for example by tearing, the periphery conductor 32 is broken, which is detected by beacon 16, causing beacon 16 to signal that packet 12 has been opened. These signals are received by a smartphone or other associated device, which can use the event as evidence that patient has taken the medication in compliance monitoring. Connection 38 of beacon 16 to central power supply 26 via the central power conductors 30 in an adjacent pack 12" allows the beacon module to stay in low power mode until removed from the packet bundle 10, without requiring communication from central beacon 34.

The electrical components and electronic features of the exemplary embodiments can be laminated between layers of the packets 12, or deposited on the inner or outer surfaces of packets 12.

Figure 5:
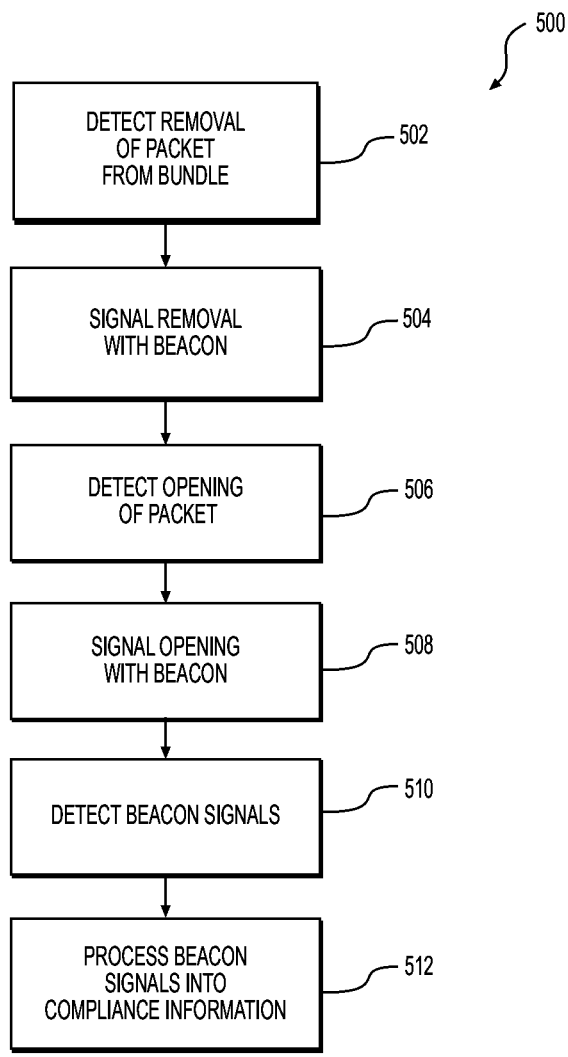
FIG. 5 is a flowchart representation of an exemplary process for obtaining compliance information from a medication packet bundle, consistent with the disclosed embodiments.

FIG. 5 shows an illustrative process 500 for obtaining compliance information from a bundle of medication packets, consistent with embodiments of the present disclosure. Process 500 may be implemented using any of the exemplary packet bundle embodiments described herein, including those illustrated and described with reference to FIGS. 2-4.

At step 502, the removal of a packet from a bundle is detected, for example through the severing of frangible conductors as discussed above. At step 504, a beacon signals removal of the packet. As discussed above, the beacon can be a central beacon connected to a plurality of packet, or a beacon associated with a single packet. Optionally, at step 506, the system detects opening of a packet. In an illustrative embodiment, this occurs through the breaking of a conductor, which is detected and at step 508 signaled by a beacon associated with the packet. At step 510, an associated device, such as a smartphone or other networked or wired device, detects beacon signals transmitted at steps 504 and optionally step 508. At step 510, one or more of the received beacon signals are processed to reveal information concerning the compliance of a patient, for example the time and date that the packet was removed, and optionally when the packet was opened, and the contents presumably taken. This information can advantageously be monitored for compliance with a medication regiment, as well as for adherence. For example, when no medication is indicated as having been taken for a period of time, it could be inferred that a prescription had not been filled.

In some embodiments, a smartphone or other device might be employed. The smartphone or device may include a controller. The controller may include one or more hardware processors, such as one or more central processing units (CPUs). The processor(s) may execute a set of instructions to perform operations, such as those of process 500 in FIG. 5. The set of instructions may be programmed and stored in one or more memory devices. Examples of memory devices include non-volatile memory (e.g., a flash memory), volatile memory (e.g., a random access memory (RAM)), and other memory components. In some embodiments, the controller may be configured run programmed instructions or software to execute operations, as described herein. The controller may also include one or more interfaces to communicate with beacons of packets or packet bundles.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have be described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed:

1. A medication package system comprising:
   a packet bundle comprising a plurality of packets of medication, each packet of the plurality of packets frangibly coupled to another packet of the plurality of packets; and
   a beacon system comprising a power source and a plurality of beacons, the power source configured to power at least one beacon of the plurality of beacons, and wherein at least one beacon of the plurality of beacons configured to transmit a signal in response to receiving a first signal generated by a breaking of a frangible coupling of a packet of medication being separated from the packet bundle.

2. The medication package system of claim 1, wherein the packet bundle comprises a plurality of packets arranged in a continuous format.

3. The medication package system of claim 2, wherein the packet bundle comprises a reel of packets.

4. The medication package system of claim 1, wherein the at least one beacon is further configured to detect an opening of the packet and transmit a second signal in response to the packet being opened.

5. The medication package system of claim 1, wherein each of the one or more beacons is affixed to a different packet of the plurality of packets of medication.

6. The medication package system of claim 1, wherein the at least one beacon is further configured to generate an interrupt based on the packet of medication being separated from the packet bundle, and the transmitting the signal is in response to the interrupt.

7. The medication package system of claim 1, wherein the at least one beacon comprises a Bluetooth beacon, and wherein the signal comprises a Bluetooth advertisement packet.

8. The medication package system of claim 7, wherein data carried by the Bluetooth advertisement packet is encrypted.

9. A method for monitoring use of a packet bundle of medication, comprising:
   detecting, by a beacon of a plurality of beacons, a packet of medication being separated from a packet bundle in response to receiving a first signal generated by a breaking of a frangible coupling of the packet of medication being separated from a packet bundle, the packet bundle comprising a plurality of packets of medication, each packet of the plurality of packets frangibly coupled to another packet of the plurality of packets; and
   transmitting, by the beacon and in response to the detection, a second signal indicating opening of the packet or separation of the packet from the packet bundle.

10. The method of claim 9, further comprising detecting the packet being opened and, in response to detecting the packet being opened, transmitting a second signal indicating the packet has been opened.

11. The method of claim 9, further comprising generating, by the beacon, an interrupt based on the packet of medication being separated from the packet bundle, and wherein the transmitting the signal is in response to the interrupt.

12. The method of claim 9, wherein the beacon comprises a Bluetooth beacon, and wherein the signal comprises a Bluetooth advertisement packet.

13. The method of claim 12, further comprising encrypting data indicating the separation of the packet from the packet bundle, and forming the Bluetooth advertisement packet including the encrypted data.

14. A medication package system comprising:
   a packet bundle comprising a plurality of packets of medication, each packet of the plurality of packets frangibly coupled to another packet of the plurality of packets; and
   a beacon system comprising a power source and a plurality of beacons, the power source configured to power at least one beacon of the plurality of beacons, and wherein at least one beacon of the plurality of beacons configured to transmit a signal in response to receiving a first signal generated by a packet of medication being opened.

15. The medication package system of claim 14, wherein the packet bundle comprises a plurality of packets arranged in a continuous format.

16. The medication package system of claim 15, wherein the packet bundle comprises a reel of packets.

17. The medication package system of claim 14, wherein each packet is separable from the packet bundle.

18. The medication package system of claim 14, wherein the at least one beacon comprises a Bluetooth beacon, and wherein the signal comprises a Bluetooth advertisement packet.

19. The medication package system of claim 18, wherein data carried by the Bluetooth advertisement packet is encrypted.

20. A method for monitoring use of a packet bundle of medication, comprising:
    detecting, by a beacon of a plurality of beacons, a packet of medication being opened in response to receiving a first signal generated by a breaking of a frangible coupling of the packet of medication being separated from a packet bundle, the packet being one of a plurality of packets of medication in a packet bundle, each packet of the plurality of packets frangibly coupled to another packet of the plurality of packets; and transmitting, by the beacon and in response to the detection, a second signal indicating the opening of the packet.

21. The method of claim 20, wherein the packet bundle comprises a plurality of packets arranged in a continuous format.

22. The method of claim 21, wherein the packet bundle comprises a reel of packets.

23. The method of claim 20, wherein each packet is separable from the packet bundle.

24. The method of claim 20, further comprising generating, by the beacon, an interrupt based on the packet of medication being opened, and wherein the transmitting the signal is in response to the interrupt.

25. The method of claim 20, wherein the beacon comprises a Bluetooth beacon, and wherein the signal comprises a Bluetooth advertisement packet.

26. The method of claim 25, further comprising encrypting data indicating the opening of the packet, and forming the Bluetooth advertisement packet including the encrypted data.

\* \* \* \* \*